United States Patent [19]
Jenkins et al.

[11] Patent Number: 4,521,225
[45] Date of Patent: Jun. 4, 1985

[54] INSTRUMENT AND PROCESS FOR TESTING LANDFILL GAS FOR CHLORINATED HYDROCARBONS

[75] Inventors: Richard L. Jenkins, Whittier; John A. Pettus, Westminster; David K. Abner, Sherman Oaks, all of Calif.

[73] Assignee: Getty Synthetic Fuels, Inc., Signal Hill, Calif.

[21] Appl. No.: 540,929

[22] Filed: Oct. 11, 1983

[51] Int. Cl.³ .............................................. B01D 15/08
[52] U.S. Cl. ........................................... 55/18; 55/67; 55/197; 55/270; 55/386; 73/23.1
[58] Field of Search ................... 55/18, 67, 71, 197, 55/270, 386; 73/23.1

[56] References Cited

U.S. PATENT DOCUMENTS

| | | | |
|---|---|---|---|
| 2,995,410 | 8/1961 | McDonell et al. | 73/23.1 X |
| 3,035,383 | 5/1962 | Sanford et al. | 55/67 |
| 3,043,127 | 7/1962 | Ford et al. | 55/67 X |
| 3,077,766 | 2/1963 | Reinecke | 73/23.1 |
| 3,095,746 | 7/1963 | Reinecke et al. | 73/23.1 X |
| 3,139,755 | 7/1964 | Reinecke et al. | 73/23.1 X |
| 3,223,123 | 12/1965 | Young | 73/23.1 X |
| 3,225,520 | 12/1965 | Burow | 55/67 |
| 3,225,521 | 12/1965 | Burow | 55/67 |
| 3,247,702 | 4/1966 | Houser et al. | 73/23.1 X |
| 3,449,938 | 6/1969 | Giddings | 55/67 X |
| 3,507,147 | 4/1970 | Llewellyn | 55/67 X |
| 3,537,297 | 11/1970 | Loyd et al. | 73/23.1 |
| 3,581,465 | 6/1971 | Haruki et al. | 55/67 |
| 3,859,209 | 1/1975 | Jahnsen et al. | 73/23.1 X |
| 3,897,679 | 8/1975 | Guild | 73/23.1 X |
| 4,470,832 | 9/1984 | Sugawara et al. | 55/197 |

FOREIGN PATENT DOCUMENTS 53-596 4/1979 Japan .................................. 73/23.1

OTHER PUBLICATIONS

Kaiser, Gas Phase Chromatography, 1963, pp. 127–142.
Keulemans, Gas Chromatography, 2nd Edition, 1960, pp. 62–64.
Basic Gas Chromatography, H. M. McNair and E. J. Bonelli, Varian Instruments Inc., pp. 1–4, 5th Edition, Mar. 1969.

Primary Examiner—Robert Spitzer
Attorney, Agent, or Firm—Gordon L. Peterson

[57] ABSTRACT

A method for determining the concentration of chlorinated hydrocarbons in landfill gas by injecting a carrier gas and landfill gas containing chlorinated hydrocarbons through a valve and into a gas chromatographic column containing a column packing capable of separating the chlorinated hydrocarbons. The temperature of the column is appropriately controlled to bring about the elution of the chlorinated hydrocarbons so that the concentration of the chlorinated hydrocarbons can be determined. The valve is a multiple port valve which permits loading of the landfill gas into the valve and subsequent injection of the landfill gas and the carrier gas into the column.

20 Claims, 4 Drawing Figures

INSTRUMENT AND PROCESS FOR TESTING LANDFILL GAS FOR CHLORINATED HYDROCARBONS

BACKGROUND OF THE INVENTION

Landfill gas, which is recovered from decomposing refuse in landfills, typically contains methane and carbon dioxide as major constituents and various impurities, such as water, nitrogen, hydrogen, chlorinated hydrocarbons and other organic compounds. By removing some, or most, of the impurities, landfill gas containing a higher percentage of methane is produced. The impurities can be removed in various different ways, including the manner disclosed in Bingham U.S. Pat. No. 4,000,990.

The chlorinated hydrocarbons are typically present in relatively small amounts in landfill gas. However, if these components are present in more than negligible concentrations, corrosive acid may form under conditions of compression and combustion. Accordingly, it is important to obtain an accurate analysis of the raw landfill gas and partly purified landfill gas so that the concentration of the chlorinated hydrocarbons in, for example, parts per million, can be accurately determined.

Unfortunately, the only equipment for accomplishing this in the prior art is a gas chromatograph-mass spectrometer. This equipment is very expensive and does not provide sufficiently accurate information as to the concentration of the chlorinated hydrocarbons.

Gas analysis for certain gases can be performed with a gas chromatograph. A conventional gas chromatograph includes a gas chromatograph column containing a column packing capable of separating the gas components and a detector for detecting the concentration of the gas components separated by the column. The gas to be analyzed is carried through the column by a suitable carrier gas. The column packing of the column may be, for example, an adsorbent which adsorbs the components of interest and separates them so that each gas component of interest is sequentially provided at the output of the column. Temperature programming of the column can be used to decrease elution time.

There is no commercially available gas chromatograph system of which we are aware that will provide the concentration of the particular chlorinated hydrocarbons found in landfill gas. More specifically, column packings that will separate the unusual list of chlorinated hydrocarbons commonly found in landfill gas are not known. Also, the particular temperature control necessary to bring about the relatively rapid separation of the chlorinated hydrocarbons is also not known.

In using of a gas chromatographic system, a sample gas can be loaded into a receiver. To inject the sample gas into the chromatographic column, a carrier gas is loaded into the receiver and allowed to carry the sample gas to the column. With landfill gas, we have found that it is sometimes desirable to use a marker gas having a composition not found in the sample and which will be separated by the chromatographic column from any of the sample components. Thus, the marker gas represents a starting point or benchmark for the detection process. The conventional gas chromatographic system provides no suitable way for injection of the marker and of the sample gas, nor does it provide a convenient manner for making redundant tests of the sample gas.

SUMMARY OF THE INVENTION

This invention provides a method and apparatus for accurately ascertaining the concentration of individual chlorinated hydrocarbons in landfill gas. Although this invention is particularly adapted to landfill gas and chlorinated hydrocarbons, it can be used to determine the concentration of chlorinated hydrocarbons in other gases.

This invention overcomes the problems noted above and adapts a relatively inexpensive gas chromatograph to detecting the concentration of chlorinated hydrocarbons in landfill gas. This invention differs from the conventional gas chromatograph system and method in several important ways. For example, this invention employs a column packing which will separate the chlorinated hydrocarbons in landfill gas. In this regard, the column packing preferably includes silica gel. In addition, the temperature of the column is controlled in a particular manner to bring about the separation of the chlorinated hydrocarbons relatively rapidly. The initial column temperature, the final column temperature, and the temperature gradient are all appropriately controlled.

Another novel feature of the invention is the use of a dual-loop injection for injecting the landfill gas or a calibration gas into the chromatographic column. The dual loop can be used, for example, to inject a landfill gas sample and a marker gas into the same column. Alternatively, dual loop may be used to inject landfill gas samples into two separate columns arranged in parallel to provide redundant testing.

The dual loop can be implemented, for example, by loading gas into first and second receivers while preventing flow of the gas in the receivers to the column and introducing a carrier gas to the receivers with the carrier gas carrying the gas from the receivers into the column. Selected components of the gas are retained in the column, and the column separates these components. The concentration of the selected components separated by the column can then be detected. The dual-loop feature is applicable to the separation of components other than chlorinated hydrocarbons.

In one form of the invention, the first and second receivers are out of communication during the loading step so that the receivers can be loaded with different gases, such as landfill gas and a marker gas. Preferably, the receivers are then coupled in series so that carrier gas can sweep through both of the receivers and carry the two gases to the column. Alternatively, the receivers can be in communication during the loading step so that they can be loaded with the same sample gas. The receivers are placed out of communication during at least a portion of the step of introducing so that the gas from the receivers is swept by the carrier gas to separate chromatographic column sections. The dual-loop functions and the receivers are preferably embodied in a multiple-port valve. Of course, more than two injection loops can be utilized, if desired.

An integral feature of the invention is the capability to calibrate the gas chromatographic system. For example, during calibration, a marker gas and a calibration standard gas can be loaded into the two receivers. The calibration standard comprises an inert gas and selected gas components in known concentration. The selected gas components of the standard gas are the same as those components which are to be detected in the sample gas.

The invention, together with additional features and advantages thereof, may best be understood by reference to the following description taken in connection with the accompanying illustrative drawing.

DESCRIPTION OF THE PREFERRED EMBODIMENTS

Figure 1:
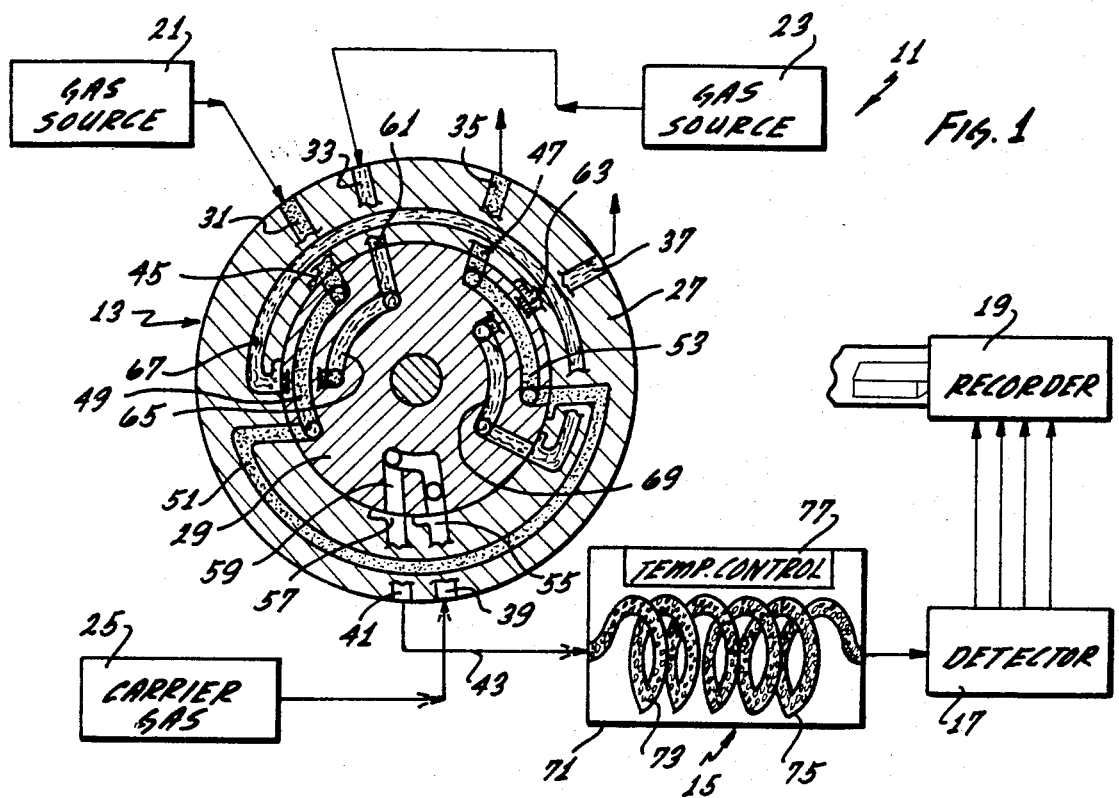
FIG. 1 is a schematic view of one form of gas chromatographic system of this invention with the dual loop injector valve being in the load position.

FIG. 1 shows a gas chromatographic system 11 which is particularly adapted for determining the concentration of chlorinated hydrocarbons in landfill gas. The system 11 includes a dual loop injector valve 13, a gas chromatographic separation module 15, a gas detector 17 and a recorder or computer 19 for recording the concentration of the chlorinated hydrocarbons as measured by the detector. The valve 13 is coupled to gas sources 21 and 23 and to a carrier gas source 25. During system operation, the gas source 21 contains landfill gas which includes methane, carbon dioxide, water, chlorinated hydrocarbons and other compounds. Specifically, the landfill gas may contain one, all or any combination of the following chlorinated hydrocarbons:

| | |
|---|---|
| Freon 11 | Freon 12 |
| Freon 21 | Freon 22 |
| Freon 113 | Freon 114 |
| Vinyl Chloride | Dichloromethane |
| Methyl Chloride | Ethyl Chloride |
| 1,1-Dichloroethene | trans-1,2-Dichloroethene |
| cis-1,2-Dichloroethene | 1,1-Dichloroethane |
| 1,2-Dichloroethane | Chloroform |
| Trichloroethene | Tetrachloroethene |
| Chlorobenzene | Carbon Tetrachloride |

Typically, landfill gas will contain most of, or all of, the above compounds, although the relative percentages of these compounds in landfill gas vary from landfill to landfill. At least ninety-five percent by volume of the chlorinated hydrocarbons found in landfill gas are typically from the above compound list.

The gas source 23 contains a source of a marker gas. The marker gas is a composition or compound not found in landfill gas and one that will be separated distinctly by the separation module 15 from the chlorinated hydrocarbons of the landfill gas. As such, the marker gas provides an easily recognizable starting point. For example, the marker gas may be 1-Bromo-2-Chloroethane.

The carrier gas provided by the carrier gas source 25 may be any of the known carrier gases. For example, inert gases, such as helium, may be used for the carrier gas.

Figure 2:
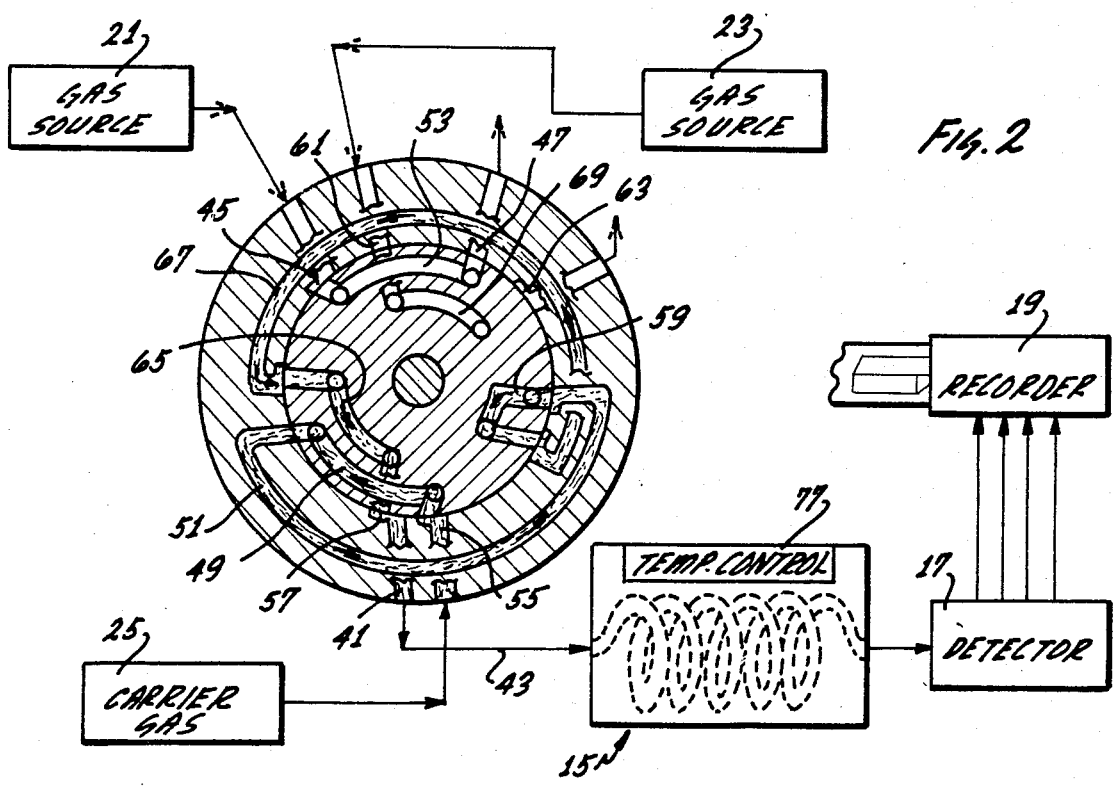
FIG. 2 is a schematic view similar to FIG. 1 with the dual loop injector valve being in the inject position.

The valve 13 is a conventional multiple port valve and is shown schematically in FIGS. 1 and 2. Although the valve 13 may be of various different constructions that will perform the desired functions, as schematically illustrated, it includes a fixed tubular member 27 and a cylindrical rotor 29 mounted for rotation within the fixed tubular member. The tubular member 27 has inlets 31 and 33 coupled to receive landfill gas and marker gas from the sources 21 and 23, respectively, and outlets 35 and 37 for returning the landfill and marker gases to their respective sources or venting these gases, if desired. In addition, the tubular member 27 has a carrier gas inlet 39 coupled to receive carrier gas from the source 25 and an outlet 41 coupled to the separation module 15 by a conduit 43.

The rotor 29 has a first port 45 and a second port 47 connectible in the load position of FIG. 1 to the source 21 of landfill gas via the inlet 31 and the outlet 35. In the load position of the valve 13 as shown in FIG. 1, the first port 45 communicates with the second port 47 through a flow path which includes a conduit section 49, a first receiver 51 and a conduit section 53.

The rotor has a third port 55 in communication with the inlet 39 to receive carrier gas and a fourth port 57 in communication with the outlet 41. In the load position of the valve 13, the third port 55 is in communication with the fourth port 57 via a conduit section 59.

The rotor 29 has a fifth port 61 in communication with the inlet 33 and a sixth port 63 in communication with the outlet 37. In the load position of FIG. 1, the ports 61 and 63 are in communication via a flow path which includes a conduit section 65, a second receiver 67 and a conduit section 69. Thus, in the load position, the landfill gas from the gas source 21 and the marker gas from the gas source 23 are loaded into the receivers 51 and 67, respectively, and the receivers 51 and 67 are out of communication with each other. Also, carrier gas can be supplied through the inlet 39, the conduit section 59, the outlet 41 and the conduit 43 to the separation module 15.

The rotor 29 of the valve 13 can be rotated clockwise from the load position of FIG. 1 to the inject position of FIG. 2. The rotor 29 is turned to the inject position after the receivers 51 and 67 have been filled with landfill gas from the source 21 and the marker gas from the source 23, respectively. In the inject position of FIG. 2, the receivers 51 and 67 are in communication with each other via the conduit section 59 and, more specifically, the two receivers are placed in series by the conduit section 59. In addition, the third port 55 communicates with the fourth port 57 through a flow path which includes the conduit section 49, the receiver 51, the conduit section 59, the receiver 67 and the conduit section 65. Accordingly, the gases in the receivers 51 and 67 can be carried by the carrier gas from the source 25 through the fourth port 57, the outlet 41, and the conduit 43 to the separation module 15. In the inject position of FIG. 2, the first port 45 is in communication with the second port 47 via the conduit section 53 so that any landfill gas supplied from the source 21 can be vented. Similarly, the fifth port 61 is in communication with the sixth port 63 through the conduit section 69 so that any marker gas supplied from the source 23 can also be vented.

The separation module 15 comprises an oven 71, column packing 73 within a suitable open column 75 and a suitable temperature controller 77. The oven 71 and temperature controller 77 may be conventional.

With this invention, the column packing 73 is capable of separating the chlorinated hydrocarbons in the landfill gas. A preferred column packing 73 includes silica gel which absorbs, adsorbs or otherwise holds and selectively releases the chlorinated hydrocarbons over a given time period. The column packing 73 selectively retards the sample components according to their distribution coefficient until they form separate bands in the carrier gas. More specifically, two preferred column packings are Chromosil 310 which comprises a liquid phase on a solid and is available from Supelco Inc. of Bellefont, Pa. and Porasil C/n-Octane which can be obtained from Waters Associates of Milford, Mass.

The column packing 73 releases each component of the landfill gas separately and at different times. The detector receives the output of the column 75 and detects the concentration of the chlorinated hydrocarbons separated by the column. The detector 17 responds only to components which contain chlorine and ignores any component which does not. The detector 17 may be conventional, and a Hall Electrolytic Conductivity Detector is preferred. Such detectors determine the concentration of the chlorinated hydrocarbons by measuring the conductivity produced from the decomposition of the component. Another suitable detector is an electron capture detector which measures the concentration of the chlorinated hydrocarbons by how well each of the components absorbs electrons.

The output of the detector 17 is a signal which represents the concentration of each of the chlorinated hydrocarbons of the landfill gas. The recorder or computer 19 is conventional and receives the signal from the detector 17 and, in response, creates a chromatogram which illustrates the marker gas and the concentration of each of the chlorinated hydrocarbons. For example, the chromatogram may comprise a peak train, with each of the peaks having characteristics, such as area or amplitude, and time, which represent the concentration and the identity of the associated chlorinated hydrocarbon, respectively.

In order to control the elution of the chlorinated hydrocarbons from the column 75, obtain the elution as fast as possible and provide for ample spacing between elution of the components, the temperature of the separation module 15, and, in particular, the column packing 73 should be appropriately controlled. The temperature conditions herein are applicable to any column packing suitable for separating and selectively eluting the chlorinated hydrocarbons found in landfill gas. The initial temperature, i.e., the temperature of the column packing 73 at the instant that landfill gas is first supplied to it, must be between 0 degrees celsius and 45 degrees celsius, and the initial temperature must be maintained for any length of time up to 60 minutes. An initial temperature less than 0 degrees celsius may degrade the performance of the column packing 73, and an initial temperature greater than 45 degrees celsius results in the early eluting components eluting together or too closely together. If the hold time for the initial temperature exceeds 60 minutes, elution time is too long and the detection peaks flatten.

The final temperature is the temperature of the column packing 73 when the last component of interest is released or eluted from the column. The final temperature should be from 45 degrees celsius to 130 degrees celsius, and the final temperature should be held or maintained for no more than 60 minutes. Of course, to hold the final temperature for a given period means that the final temperature was reached such given period before the last component of interest is eluted from the column. If the final temperature is below 45 degrees, elution takes too long and, if the final temperature is above 130 degrees celsius, the column packing tends to deteriorate. If the final temperature is held for more than 60 minutes, elution takes too long.

In moving from the initial temperature to the final temperature, a temperature gradient of 3 degrees celsius per minute plus or minus 2 degrees celsius per minute should be used. In other words, the temperature gradient can vary from 1 degree celsius per minute up to 5 degrees celsius per minute. The temperature gradient can vary as the temperature increases from the initial temperature to the final temperature, i.e., be nonlinear. A temperature gradient above 5 degrees celsius per minute causes some components to elute together and a temperature gradient below 1 degree celsius per minute increases elution time and makes the detection of component concentration more difficult.

The preferred initial temperature is between 25 degrees celsius and 38 degrees celsius, and this initial temperature is preferably held from 15 to 30 minutes. The final temperature is preferably between 75 and 130 degrees celsius and is held for 18 minutes. The preferred temperature gradient is from 2 to 3 degrees celsius per minute. The conditions regarded as optimum are an initial temperature of 33 degrees celsius, a hold time of 20 minutes for the initial temperature, a temperature gradient of 2.5 degrees celsius per minute, a final temperature of 75–130 degrees celsius and a hold time at the final temperature of 18 minutes.

The temperature controller 77 can be operated mechanically or automatically to achieve the desired temperature program. For convenience, the temperature which is controlled is the air temperature within the oven 71.

To calibrate the system 11, the receiver 51 is loaded with a calibration standard from a source (not shown) coupled to the inlet 31, and the receiver 67 is loaded with a marker gas from the source 23. The valve 13 is then placed in the inject position so that the carrier gas can carry the calibration standard and the marker gas into the column 75. The calibration standard comprises an inert gas and all of the chlorinated hydrocarbons of the landfill gas. The components of the marker gas and the calibration standard are eluted separately by the column 75, and the concentration of the chlorinated hydrocarbons is detected by the detector 17 and recorded by the recorder 19. Because the calibration standard has known concentrations of selected chlorinated hydrocarbons, the identification of a particular chlorinated hydrocarbon and its concentration are determined, respectively, from the elution time and peak area which are generated by the recorder or computer. The marker gas serves its usual marking or starting purpose in the calibration process.

Following calibration, landfill gas from the source 21 and marker gas from the source 23 can be loaded into the valve 13 and thereafter injected into the column 75. The temperature within the separation module 15 is controlled, as described above, to bring about the separation of the marker gas and the chlorinated hydrocarbons. The detector detects the concentration of the chlorinated hydrocarbons released from the column 75, and the concentration of these components is recorded by the recorder 19.

Figure 3:
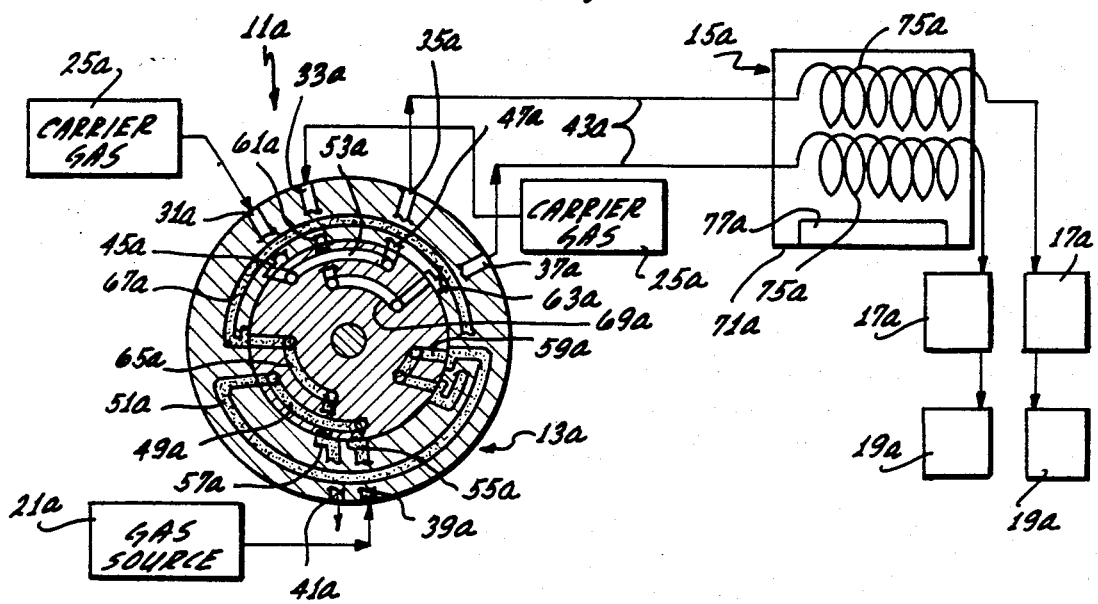
FIG. 3 is a schematic view similar to FIG. 1 of a second embodiment of gas chromatographic system with the dual loop injector valve being in the load position.
Figure 4:
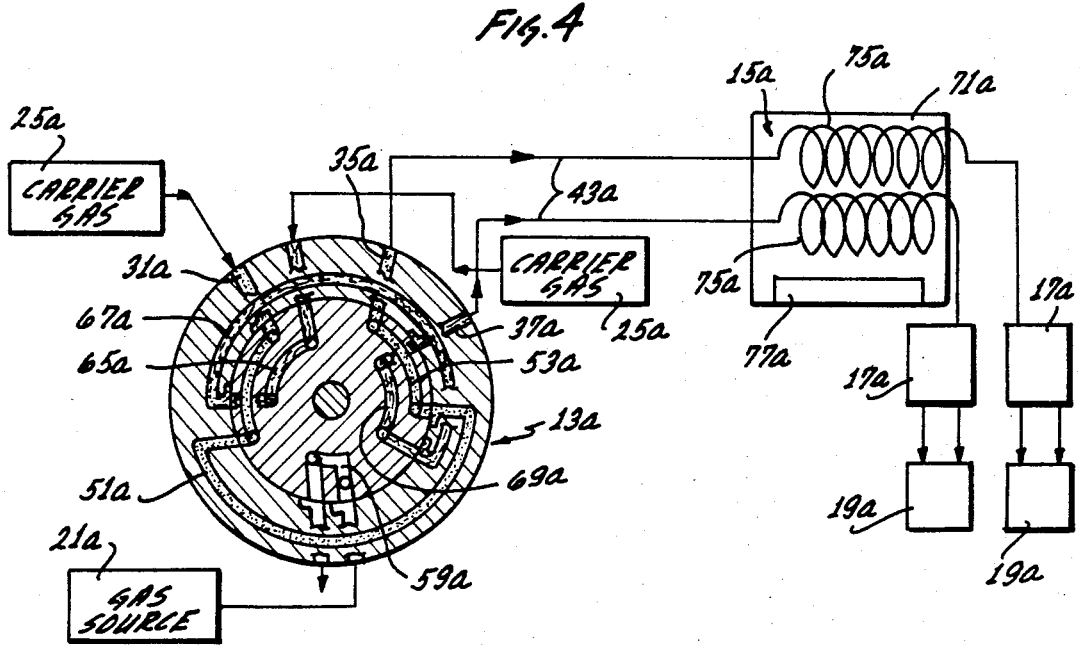
FIG. 4 is a schematic view similar to FIG. 3 of the second embodiment of the invention with the dual loop injector valve being in the inject position.

FIGS. 3 and 4 show a system 11a which is identical to the system 11 in all respects not shown or described herein. Portions of the system 11a corresponding to portions of the system 11 are designated by corresponding reference numerals followed by the letter "a."

The system 11a differs from the system 11 in that the chromatographic separation module 15a of the former has two columns 75a within the oven 71a and each contains column packing. In addition, with the system 11a, there are two sources of carrier gas 25a coupled to the inlets 31a and 33a, respectively, and the outlets 35a and 37a are coupled to conduits 43a which lead to the two columns 75a, respectively. With the system 11a, there is no source of marker gas. However, the gas source 21a of landfill gas is coupled to the inlet 39a and the outlet 41a.

The valve 13a is identical to the valve 13. However, in the load position of the valve 13a, the valve components are in the same position as the inject position for the valve 13.

In the load position of FIG. 3, carrier gas from one of the sources 25a is supplied through the inlet 31a, the port 45a, the conduit section 53a, the port 47a, the outlet 35a and one of the conduits 43a to one of the columns 75a. Similarly, carrier gas from the other source 25a is supplied through the inlet 33a, the outlet 37a and the other of the conduits 43a to the other of the columns 75a. Simultaneously, landfill gas flows from the source 21a through the inlet 39a, the conduit section 49a, the receiver 51a, the conduit section 59a, the receiver 67a, the conduit section 65a, the port 57a, and the outlet 41a to the atmosphere through a vent. Thus, in the load position, the receivers 51a and 67a are connected in series by the conduit section 59a, and both of them are out of communication with the columns 75a.

In the inject position of FIG. 4, the valve 13a is in the same position that the valve 13 occupies in the load position (FIG. 1). Thus, the receivers 51a and 67a are placed in communication with the carrier gas sources 25a, and the landfill gas stored in the receiver 51a is swept by the carrier gas through the outlet 35a and one of the conduits 43a to one of the columns 75a. Similarly, the landfill gas stored in the receiver 67a is swept by the carrier gas from the other carrier gas source 25a out the outlet 37a and the other of the conduits 43a to the other of the columns 75a.

Each of the columns 75a may be identical to the column 75 (FIG. 1) in that they include a column packing capable of separating and selectively releasing the chlorinated hydrocarbons of the landfill gas. The output from the columns 75a is fed to separate detectors 17a and to separate recorders 19a. Accordingly, the single system 11a provides for redundant testing of the landfill gas. Of course, in both embodiments of the invention, the various gas sources may be appropriately valved to shut off flow from these sources when desired.

Although exemplary embodiments of the invention have been shown and described, many changes, modifications and substitutions may be made by one having ordinary skill in the art without necessarily departing from the spirit and scope of this invention.

We claim:

1. A method for determining the concentration of chlorinated hydrocarbons in landfill gas comprising:
    injecting a carrier gas and landfill gas containing a plurality of chlorinated hydrocarbons into a gas chromatographic separation module which includes a column containing a column packing capable of separating the chlorinated hydrocarbons;
    controlling the temperature of the separation module to separate the chlorinated hydrocarbons from the separation module;
    said step of controlling including providing an initial temperature of 0 to 45 degrees celsius for no more than 60 minutes, increasing the initial temperature at a rate of 1 to 5 degrees celsius per minute to a final temperature of from 45 to 130 degrees celsius and holding the final temperature for no more than 60 minutes; and
    detecting the concentration of the chlorinated hydrocarbons separated by the column packing.

2. A method as defined in claim 1 wherein said step of controlling provides the initial temperature in the range of 25 to 38 degrees celsius from 15 to 30 minutes, increasing the initial temperature at a rate of 2 to 3 degrees celsius per minute to a final temperature of 75 to 130 degrees celsius.

3. A method as defined in claim 1 wherein said step of controlling includes providing an initial temperature of about 25 to 38 degrees celsius.

4. A method as defined in claim 1 wherein said step of controlling includes increasing the temperature from the initial temperature to the final temperature at about 2 to 3 degrees celsius per minute.

5. A method as defined in claim 1 wherein said step of controlling includes providing a final temperature of about 75 to 130 degrees celsius.

6. A method as defined in claim 1 wherein the initial temperature is about 33 degrees celsius and held for about 20 minutes, said final temperature is from about 75 to 130 degrees celsius and held only for about 18 minutes and the temperature is increased from the initial temperature to the final temperature at about 2.5 degrees celsius per minute.

7. A method as defined in claim 1 wherein said column packing includes silica gel.

8. A method for determining the concentration of selected components of a gas using a chromatographic separation module which includes a chromatographic column and a column packing in the column, said method comprising:
    loading gas into first and second receivers while preventing flow of the gas in the receivers to the chromatographic column;
    introducing a carrier gas to the receivers with the carrier gas carrying the gas from the receivers into the chromatographic column;
    separating the selected components of the gas with the chromatographic column; and
    detecting the concentration of the selected components separated by the column.

9. A method as defined in claim 8 including maintaining the first and second receivers out of communication during said step of loading, said step of loading includes loading first and second gases into the first and second receivers, respectively, and providing communication between said first and second receivers during at least a portion of said step of introducing whereby the first and second gases are carried by the carrier gas to the chromatographic column.

10. A method as defined in claim 9 wherein said first gas contains said selected components and said second gas is a marker which contains none of said selected components.

11. A method as defined in claim 9 wherein said first gas is landfill gas and the selected components are chlorinated hydrocarbons.

12. A method as defined in claim 8 including maintaining the first and second receivers in communication during said step of loading, maintaining said first and second receivers out of communication during at least a portion of said step of introducing, said chromatographic column is a first chromatographic column and the separation module includes a second chromatographic column containing a column packing and said step of introducing introduces the carrier gas to the first and second receivers with the carrier gas carrying the gas from the first and second receivers into the first and second chromatographic columns, respectively, said step of separating includes separating the selected components of the gas with each of said chromatographic columns, columns and said step of detecting includes detecting the concentration of the selected components separated by the first and second chromatographic column.

13. A method as defined in claim 8 wherein the gas includes landfill gas and the selected components are chlorinated hydrocarbons.

14. A method as defined in claim 13 including controlling the temperature of the column to selectively release the chlorinated hydrocarbons from the chromatographic column, said step of controlling includes providing an initial temperature of 0 to 45 degrees celsius for no more than 60 minutes, increasing the initial temperature at a rate of 1 to 5 degrees celsius per minute to a final temperature of from 45 to 130 degrees celsius and holding the final temperature for no more than 60 minutes.

15. A gas chromatographic system for determining the concentration of selected components of a gas, said gas chromatographic system comprising:
    first and second gas receivers adapted to receive and hold a volume of gas;
    first and second conduit means for supplying the first and second receivers, respectively, with gas;
    means for terminating the supply of the gas through the first and second conduit means to the first and second receivers;
    connecting conduit means for providing communication between the first and second receivers;
    means for terminating the communication through the connecting conduit means between the first and second receivers;
    a gas chromatographic column and a column packing in the column capable of separating the selected components;
    means for detecting the concentration of the selected components separated by the column packing;
    third conduit means for coupling the gas receivers to the chromatographic column;
    means for terminating the communication between the receivers and the chromatographic column through said third conduit means;
    fourth conduit means for supplying a carrier gas to the receivers; and
    means for terminating the supply of the carrier gas through the fourth conduit means to the receivers whereby the supplying of the carrier gas to the receivers can be controlled and the carrier gas can carry the gas from the receivers to the column.

16. A gas chromatographic system as defined in claim 15 wherein said connecting conduit means couples the first and second receivers together in series, and the fourth conduit means supplies the carrier gas to the first receiver.

17. A gas chromatographic system as defined in claim 15 wherein said column packing comprises a material capable of separating chlorinated hydrocarbons.

18. A gas chromatographic system as defined in claim 15 wherein said gas chromatographic column is a first chromatographic column, the system includes a second chromatographic column, and said third conduit means couples the first and second receivers to the first and second chromatographic columns, respectively.

19. A gas chromatographic system for determining the concentration of chlorinated hydrocarbons in landfill gas, said gas chromatographic system comprising:
    a valve including first and second ports connectible to a source of the landfill gas, first conduit means including at least a first receiver, a third port connectible to a source of carrier gas, and a fourth port;
    said valve including fifth and sixth ports connectible to a source of a second gas and second conduit means including a second receiver;
    said valve having a load position in which said first and second ports are in communication through a flow path which includes said first conduit means and said first receiver and said fifth and sixth ports are in communication through a flow path which includes the second conduit means and the second receiver whereby the landfill gas and the second gas can be loaded into the first and second receivers, respectively, and an inject position in which the third and fourth ports are in communication through a flow path which includes the first and second receivers whereby the gases in the receivers can be carried by the carrier gas through the fourth port;
    a gas chromatographic column and a column packing within the column capable of separating the chlorinated hydrocarbons in the landfill gas;
    conduit means for coupling the fourth port to the column whereby the column can receive the carrier gas, the landfill gas and the second gas from the fourth port; and
    means for detecting the concentration of the chlorinated hydrocarbons separated by the column packing.

20. A gas chromatographic system for determining the concentration of chlorinated hydrocarbons in landfill gas, said gas chromatographic system comprising:
    a valve including first and second ports connectible to a source of the landfill gas, first conduit means including at least a first receiver, a third port connectible to a source of carrier gas, and a fourth port;
    said valve including a fifth port connectible to a source of the carrier gas, a sixth port, and a second receiver;
    said valve having a load position in which said first and second ports are in communication through a flow path which includes said first and second receivers whereby the landfill gas can be loaded into the first and second receivers and an inject position in which the third and fourth ports are in communication through a flow path which includes the first receiver and said fifth and sixth ports are in communication through a flow path which includes said second receiver whereby the landfill gas in the receivers can be carried by the carrier gas through the fourth and sixth ports;

first and second gas chromatographic columns each having a column packing therein capable of separating the chlorinated hydrocarbons of the landfill gas;

conduit means for coupling the fourth and sixth ports to the first and second columns, respectively, whereby the columns can receive the carrier gas and the landfill gas; and means for detecting the concentration of the chlorinated hydrocarbons separated by the columns.

* * * * *